United States Patent
Schima et al.

[11] Patent Number: 6,155,969
[45] Date of Patent: Dec. 5, 2000

[54] CENTRIFUGAL PUMP FOR PUMPING BLOOD AND OTHER SHEAR-SENSITIVE LIQUIDS

[75] Inventors: Heinrich Schima, Körnergasse 7/9, A-1020 Vienna; Helmut Schmallegger, Vienna, both of Austria

[73] Assignees: Kyocera Corporation, Kyoto, Japan; Heinrich Schima, Vienna, Austria

[21] Appl. No.: 09/230,125
[22] PCT Filed: Jul. 23, 1997
[86] PCT No.: PCT/AT97/00173
  § 371 Date: Mar. 9, 1999
  § 102(e) Date: Mar. 9, 1999
[87] PCT Pub. No.: WO98/04834
  PCT Pub. Date: Feb. 5, 1998

[30] Foreign Application Priority Data

Jul. 29, 1996 [AT] Austria .................... 1357/96

[51] Int. Cl.⁷ .................................................. A61M 1/10
[52] U.S. Cl. ............................................................. 600/16
[58] Field of Search ........................................... 600/16, 17

[56] References Cited

U.S. PATENT DOCUMENTS

| | | | |
|---|---|---|---|
| 5,470,208 | 11/1995 | Kletschka | 600/16 |
| 5,503,615 | 4/1996 | Goldstein et al. | 600/16 |

FOREIGN PATENT DOCUMENTS

| | | |
|---|---|---|
| 42 40 718 A1 | 6/1993 | Germany . |
| 196 13 388 | 10/1996 | Germany . |
| WP 92/03181 | 3/1992 | WIPO . |
| WO 95/00185 | 1/1995 | WIPO . |

*Primary Examiner*—William E. Kamm
*Attorney, Agent, or Firm*—Herbert Dubno

[57] ABSTRACT

The invention relates to a centrifugal pump comprising a pump head (1) and a drive (2) for delivering blood and other ?-sensitive fluids, such as cell-containing cleaning suspensions, for example, in blood-cleaning units, wherein the drive (2) has a drive rotor (64) with a rotor disk (8) which is provided with permanent magnets (7) which are assigned permanent magnets (33), fitted on the pump rotor (3), for the purpose of magnetic coupling, and are assigned in the drive to the magnetic coils (4) of a stator for the purpose of generating the rotary movement, and wherein the pump rotor axis (61) extends into the pump intake (11) and is magnetically centered in the pump intake (11).

23 Claims, 7 Drawing Sheets

Schnitt F-F

CENTRIFUGAL PUMP FOR PUMPING BLOOD AND OTHER SHEAR-SENSITIVE LIQUIDS

The present invention relates to a centrifugal pump comprising a pump head and a drive for delivering blood and other shear-sensitive fluids, such as cell-containing cleaning suspensions, for example, in blood-cleaning units.

Increasing use is being made of centrifugal pumps for delivering sensitive fluids which can change in their composition owing to excessive friction and shear stress. Particularly in medical and biological applications, such pumps are used, For example, for heart-lung machines, for supporting the failing heart, as well as for purpose of blood preparation for suspensions of cells or biologically active particles. In this case, the rotor of the pump is mostly driven via a conventional motor, it being the case either that the energy is injected into the magnets of the pump rotor via an additional magnet disk of the drive, or that the magnets of the pump rotor are lengthened in the axial direction and are therefore arranged as rotor of electric motor in the rotary field of the stator. Combinations of disk-rotor motors with magnetic couplings have also been described (for example EP-401 761-A2, Ebara Corp.), but they also provide for structural separation of the magnetic circuits of the rotor and the pump. These arrangements entail a substantial overall height of the pump, and this is disadvantageous.

Particularly in the case of blood pumps for cardiac support, which can be implanted or are fitted near the body, but also in the case of bedside mounted units for blood purification and in other applications, the aim is a pump/drive combination of low overall height and of low volume and weight. A pump of low design is proposed in the PCT application WO-92/03 181-A1, Baylor College. In this pump, the magnetic disk driven by the disk-rotor stator is used simultaneously for the magnetic coupling of the rotor. In the case of a motor of this design, a considerable volume of iron is required for the magnetic return path and, at the same time, a relatively low magnetic saturation is achieved. A pump has become known (via Schima et al., Artificial Organrs 19:7 (1995), Pages 639–643) in which coupling of the magnetic circuits of the motor and pump rotor is performed. However, with this arrangement the rotor is stabilized by three supporting points on the pump base, and this can lead to increased blood traumatization during the conveyance of blood. Furthermore, a pump has become known (Yamane et al: Artificial Organs 19:7 (1995), Pages 625–630) in which there is a magnetic suspension of the rotor on the tip facing the intake, fit being the case there, however, that because of the unfavorable distribution of the magnetic forces the overall height must be relatively large and the intake is disturbed. Finally, mention may be made of a centrifugal pump (Akamatsu et al: Artificial Organs 19:7 (1995), Pages 631–634), in which in addition to the magnetic injection of the rotational energy via additional magnet disks, electromagnetic stabilization of the rotor is provided by complete floating in the housing. However, this stabilization requires a relatively large coil apparatus on the circumference of the pump.

It is the object of the present invention to create and improve the pump of the type described at the beginning and the drive therefore, in which the existing disadvantages are avoided. In particular, the pump is intended to have a low overall height and low volume and weight, as well as a high operational reliability. The unfavorable mechanical effects on the delivered medium, such as high shear forces, are to be avoided.

The present invention is defined by virtue of the fact that the drive has a drive rotor with a rotor disk which is provided with permanent magnets which are assigned permanent magnets, fitted on the pump rotor, for the purpose of magnetic coupling, and are assigned in the drive to the magnetic coils of a stator for the purpose of generating the rotary movement, and in that the pump rotor axis extends into the pump intake and is magnetically centered in the pump intake.

According to a further characteristic of the invention, for the purpose of magnetically centering the pump rotor axis the latter has a permanent magnet, and the pump intake has one or more annularly arranged magnets polarized in the same direction. The magnets can be permanent magnets or electromagnets. The magnets can preferably be arranged in the wall of the pump intake, an annular flow channel being formed between the pump rotor axis and the wall of the pump intake. The permanent magnet on the pump rotor axis or the pump rotor can be offset in the axial direction with respect to the annularly arranged magnets of the pump intake, in order to increase the centering effect. Controls are arranged on the wall of the pump intake or on the pump rotor axis, magnets or their yoke projecting if appropriate into the region of the control surfaces. One or both magnets of the pump intake can have oblique or contoured surfaces on their sides facing one another.

In accordance with the preferred feature of the invention, the bearing of the pump rotor is constructed as a magnetic bearing on the rear wall of the pump head, this bearing comprising one or more permanent magnets In the rear rotor tip on the rear side of the rotor and permanent magnets and/or electromagnets in the bearing shell formed by the rear wall. The bearing of the pump rotor on the rear wall of the pump head can be constructed as a magnetic bearing, on the rear wall of the pump head, this bearing comprising one or more permanent magnets in the rear rotor tip on the rear side of the rotor and permanent magnets and/or electromagnets in the bearing shell formed by the rear wall. Alternatively, the bearing seat of the pump rear wall can be designed with a flat central surface for the rear rotor tip, which surface permits lateral excursions of the rear rotor tip in a limited range of typically 0.5 to 3 mm diameter.

According to further features, the pump rotor has on its rear side vanes which during rotation produce a dynamic pressure by virtue of a different inclination of the vane surfaces on the upstream side and downstream side, and thereby facilitate and/or cause lifting of the pump rotor from the rear wall. The pump rotor can be designed with exposed rotor vanes in which there are recessed magnets whose magnetization runs transverse to the rotation axis of the pump rotor axis. There can be provided on the underside of the rotor vanes support surfaces which cause an axial force during rotation in fluid. There can be provided on the topside of the rotor vanes support surfaces which cause an axial force during rotation in fluid.

The rotor vanes can have different surfaces and/or angles of attack, and thereby cause an asymmetrical flow on the rear wall of the pump.

The drive itself can be advantageously constructed in several ways. According to one variant, the drive rotor comprises an upper and a lower rotor disk and the magnet coils of the stator are situated between the two rotor disks. For the purpose of reducing the stray magnetic field the lower rotor disk of the drive can have a magnetic return path in the form of a magnetically conductive disk or ring made, for example, from soft iron. For the purpose of improving the efficiency of the drive the coils can be arranged in a plurality of offset layers and/or wound inclined to the plane of the coil form. Alternatively, the drive rotor can comprise an upper rotor disk, and provided in the stator instead of the lower rotor disk is a magnetic yoke which interconnects the iron cores of the magnet coils of the stator. To prevent or reduce eddy currents, circular and/or radial depressions or also slots can be provided in the rear wall of the pump or, in the case of a separable pump and drive, on the covering wall of the drive.

According to a further feature, it is provided that in each case a pump head is fitted on both sides of the drive in the axial direction, preferably for the purpose of simultaneously supporting/substituting left-hand and right-hand halves of the heart, it being possible for the size and rotor configuration of the two pump heads to differ in order to achieve a pumping capacity matched to the physiological requirements. The pump head and the drive are preferably separated from one another in order to replace the pump head or the drive alone.

The advantageous features and improvements relate both to the pump itself and to its drive and are constitute an advantageous invention both separately from one another and in combination.

The invention will be explained below in more detail with the aid of the drawings.

FIG. 2c shows, by way of example, the rear view of a rotor without a closed rear wall, with exposed vanes and magnets integrated therein.

Figures 1, 2A:
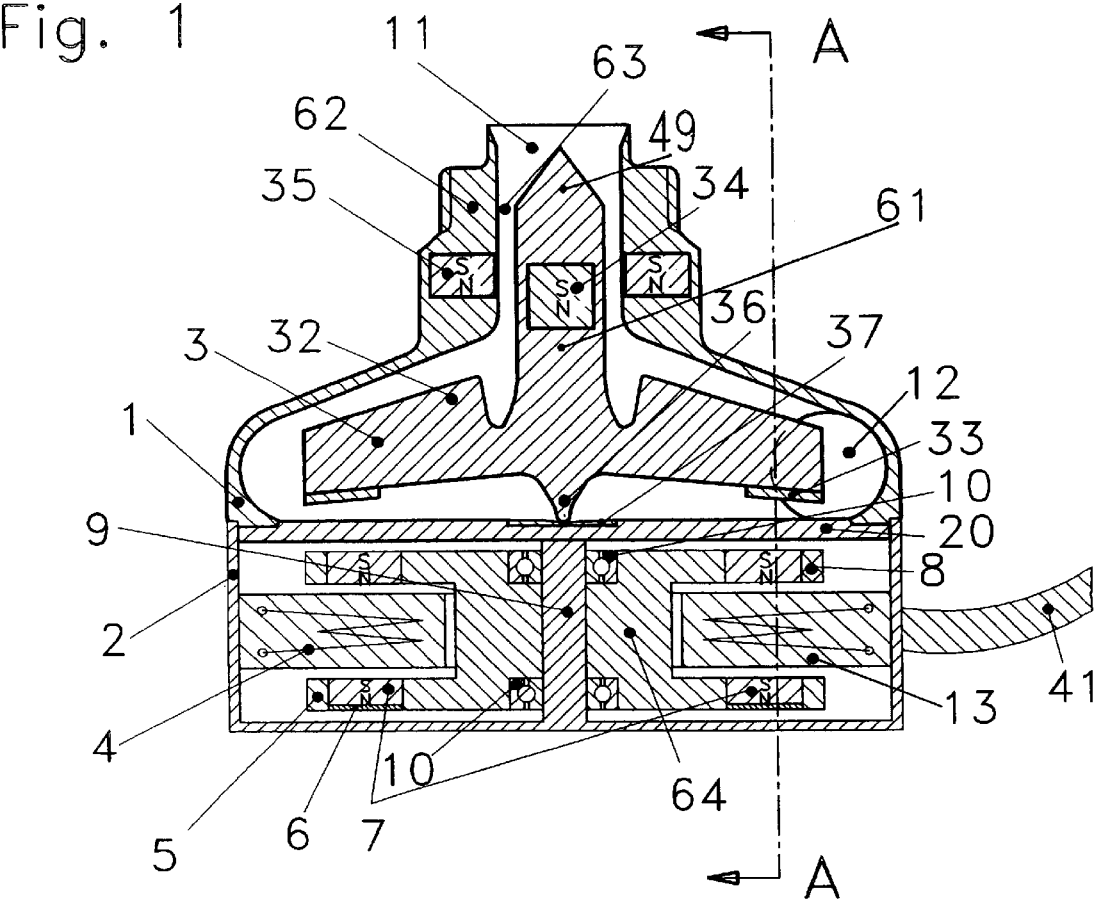
FIG. 1 shows a first embodiment of the pump according to the invention.
FIGS. 2a, 2b, 2c and 3 are sections along the line A—A through the pump, with a different design of the rotor and the stator windings, the housing parts having been left out to improve clarity.

As FIG. 1 shows in cross-section, the pump head 1 contains a pump rotor 3 with rotor blades 32, which causes the fluid entering the pump head through the pump intake 11 to rotate and presses it through the pump outlet 12 by means of the centrifugal force produced by the rotation.

The rotary movement of the pump rotor 3 is injected via a magnetic field. Both the pump rotor 3 and the two rotor disks 5, 8 of the drive rotor 64 of the drive 2 have permanent magnets (drive magnets 7, 33), the drive magnets 7 of the motor rotor disks 5, 8 being in each case alternately differently polarized. In this case, use is preferably made of 6, 12, 18 or 24 magnets per disk. Rotor disks 5, 8 of the drive 2 are arranged rotatably, either the axis 9 being rotatable, or the two rotor disks 5, 8 being mounted on a fixed axis 9 via one or more bearings 10. Arranged between the two rotor disks 5, 8 is a stator or coil form 13 with magnet coils 4 which are connected via the supply lead 41 to the electric rotary field, and thereby generate the electromagnetic motor rotary field. The required commutation of the electric field is preferably performed by means of an electronic circuit in a known way by evaluating the backward EMF, it being possible for this circuit also to be integrated into the drive itself.

The magnets 33 in the pump rotor can be arranged either parallel to the drive magnets 7 of the drive 2, or, preferably as represented in FIG. 2a, be arranged transverse to the drive magnets 7 for the purpose of reducing the forces acting laterally on the pump rotor 3. The magnetic field lines 44, and thus the forces, then act to a considerable extent transverse to the bearing axis, the tilting torque being substantially reduced as a result.

Figure 2B:
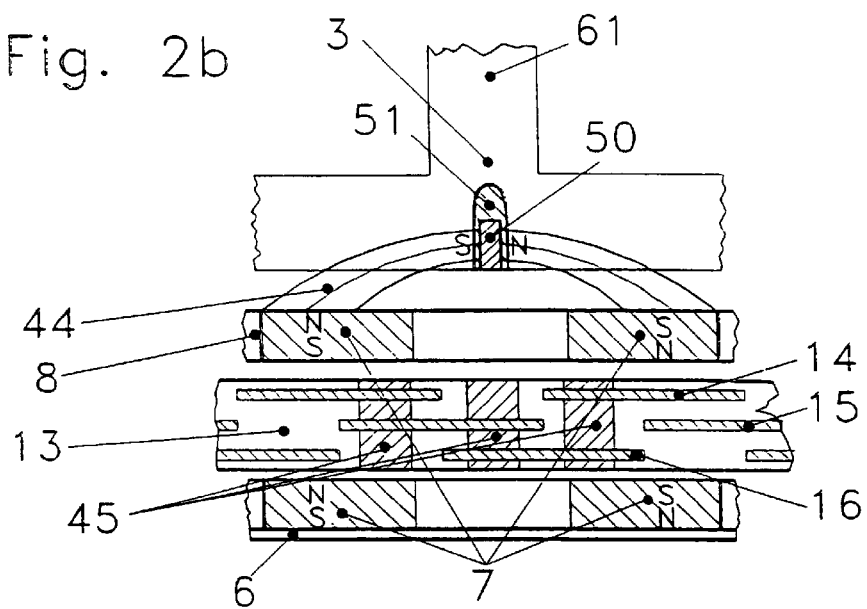
Figure 3:
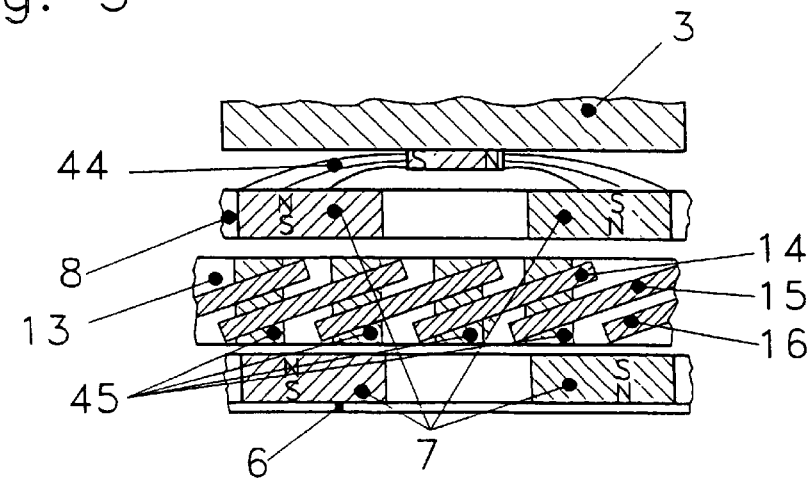

The coils 14, 15, 16, shown in FIGS. 2a and 2b and 3, of the coil form 13 can either be situated next to one another or, as shown in FIG. 2a, be arranged in a plurality of layers offset one above another or, as shown in FIG. 3, be arranged in an obliquely overlapping fashion. Iron cores or beds of iron cores 45 can be provided in order to increase the magnetic flux.

Figure 2C:
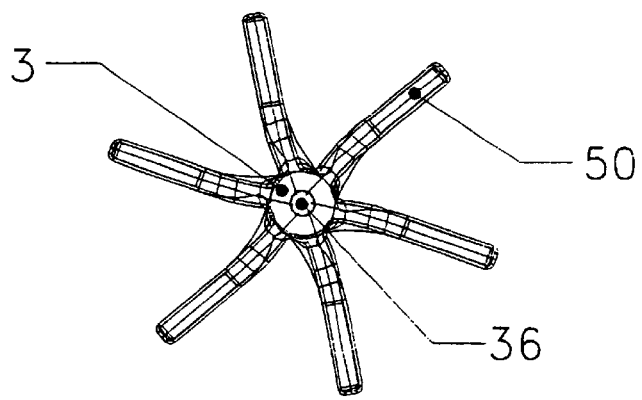

As represented in FIG. 1, in order to ensure as high as possible a field strength of the field generated by the permanent magnets 7, and thus to ensure good efficiency for the motor, it is possible to arrange below the permanent magnets of the lower rotor disk 5 a disk or ring 6 made from soft iron, which minimize the stray fields on the rear side of the drive 2 and over the pump rotor 3. If the magnets 33 of the pump rotor are arranged in the same direction as the drive magnets 7, it is also possible for a soft iron disk or soft iron ring to be arranged over them for the magnetic return path. As represented in FIGS. 2b and 2c, the pump rotor 3 can, however, also be designed with exposed vanes 51 into which magnets 50 for magnetizing transverse to the axis are recessed.

Figure 4:
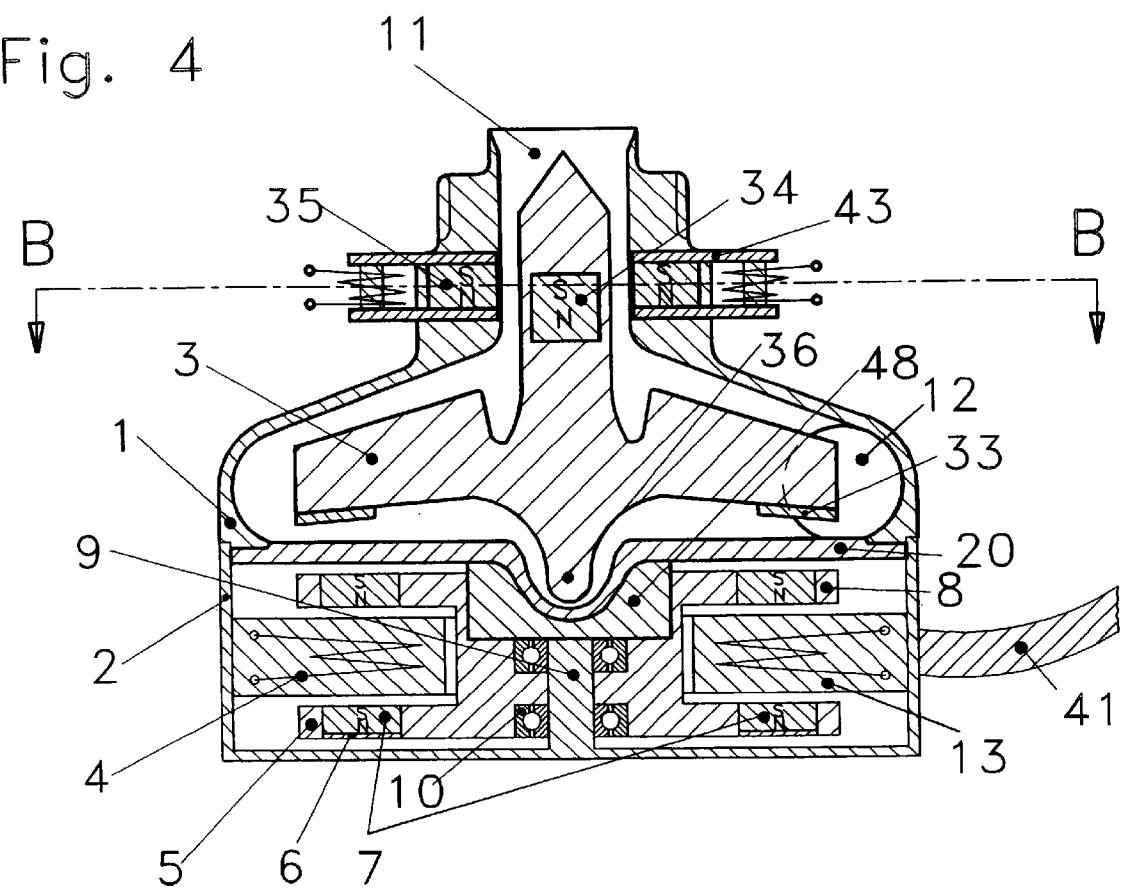
FIG. 4 shows an embodiment with electromagnets, a detailed view relating to the bearing of the rotor tip in the rear wall of the pump being given in FIG. 5.
Figure 9:
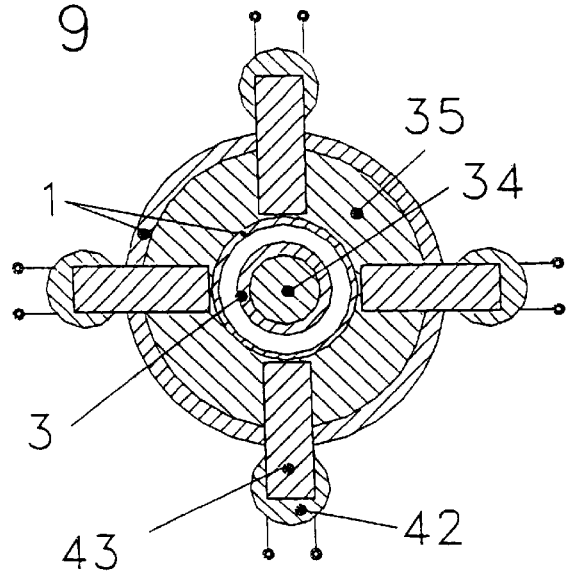
FIG. 9 shows an embodiment of electromagnets on the rotor tip for FIG. 4.

The pump rotor 3 is mounted magnetically in the intake. Accommodated for this purpose on its pump rotor axis 61 or rotor tip 49 thereof is a permanent magnet 34 opposite which there is situated around the intake 11 an annular magnet arrangement 35 polarized essentially in the same direction. As represented in FIG. 1, this magnet 35 is preferably designed as a purely permanent magnet. As shown in FIG. 4 and FIG. 9, however, it is also possible to provide additional, electromagnetic coils 42 with iron yokes 43, for the purpose of improving the stabilization. The magnets 35 are preferably arranged in the wall 62 of the pump intake 11, in order not to impede the intake through the annular flow channel 63.

Figure 5:
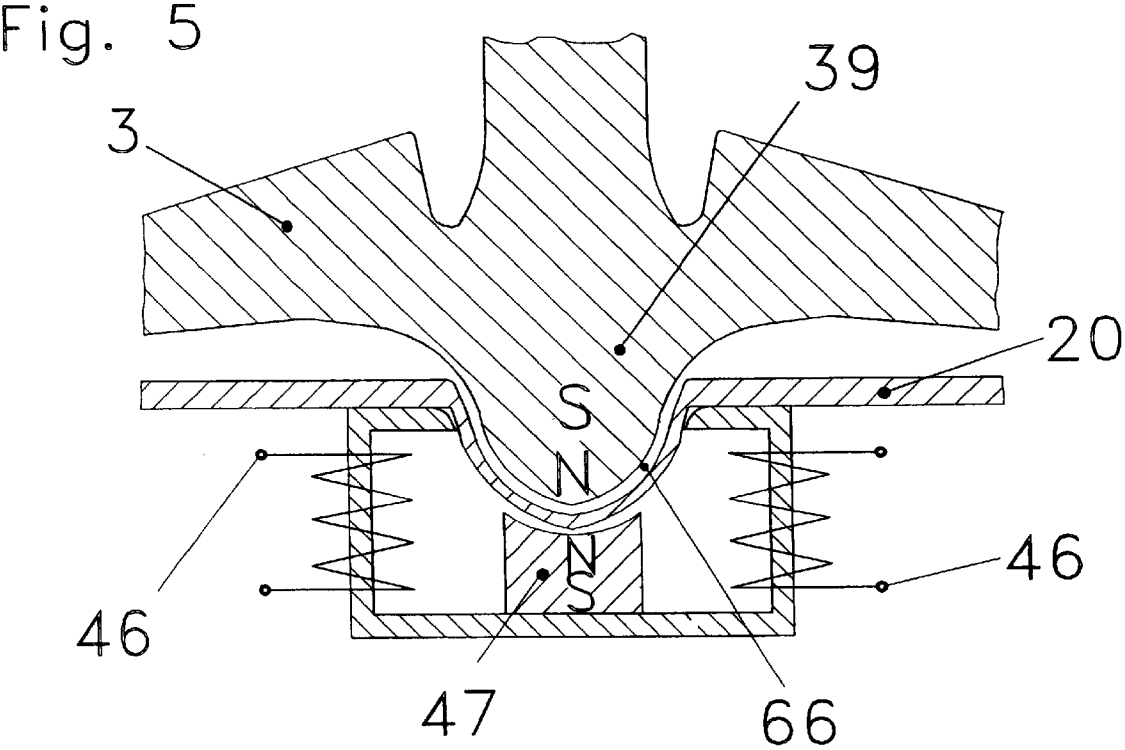

The bearing on the rear wall 20 of the pump head can be designed as a pivot bearing (FIG. 1). In order to lower the friction and thus the heat and destruction of blood produced at the bearing tip 36 in the bearing shell 37, it is possible, moreover, to provide a partial or complete magnetic bearing 48. FIG. 5 shows a possible design of this magnetic bearing, which has a permanent magnet 39 in the rear rotor tip and has electromagnetic coils 46 in the bearing shell and, additionally, can have a permanent magnet 47. The checkback signal For the magnet position can be determined in this case either from the impedance of the coils 46 or by position sensors.

Figure 10:
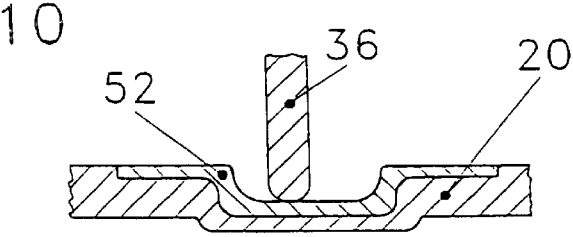
FIG. 10 shows an embodiment of the rear rotor tip in a bearing without centering function.

As FIG. 10 shows, the lower rotor bearing can also be designed with a flat bearing seat 52 in which the bearing tip 36 of the rotor rear side can execute transverse movements within a certain range without mechanical limitation, in order to permit the bearing seat to be cleaned automatically of blood constituents, there being a need to provide a flat region of typically 0.5 to 3 mm diameter. The bearing seat 52 can preferably be made in this case from ceramic or high-density plastic.

Figure 7:
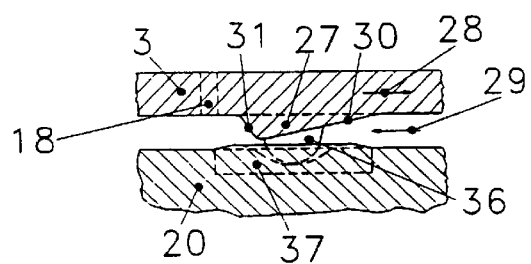
FIG. 7 represents a detail of a side view of the side of a rotor with rear wall.
Figure 8:
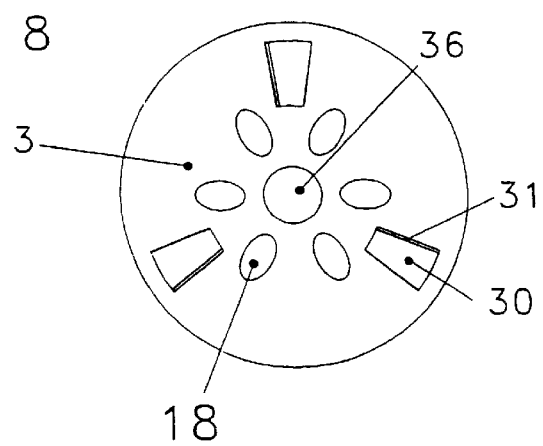
FIG. 8 represents the rear view of this rear wall.

As shown in FIG. 7 in the side view of the rotor rear side, and in FIG. 8 in a plan view thereof, it is possible to fit on the rear side of the pump rotor 3 7,vanes 27 whose shape facilitates controlled lifting of the rotor from the pump rear wall 20 and the middle piece thereof. Because of the rotation 28 of the pump rotor 3, the incoming fluid 29, which strikes the vanes 27 produces a dynamic pressure on the flat inclined upstream side, while low corresponding counter-pressure is built up on the steeply set rear side 31 of the vanes. This makes it easy for the rotor to run up on a liquid layer of controlled thickness (depending on the speed, the counter-pressure, the viscosity of the liquid and the spacing of the vanes 27 from the rear wall 20 of the pump head 1), and minimizes the force to be absorbed by the magnet bearings. Moreover, this equalization of the different pressures on the rotor underside and topside can be performed by recesses 18 in the pump rotor or by shaping the rotor in self-supporting vanes.

Furthermore, either an asymmetrical configuration of the permanent magnet 47 (FIG. 5) or a bipartite outlet can be provided for equalizing the forces on the circumference of the rotor, which act eccentrically in the case of a single outlet.

In order to render possible multiple use of the drive in the case of pump heads which are to be used only once, or in the case of replacement of the pump head, the pump head and drive can be designed separately from one another, as represented in FIG. 1. For use with cell-containing fluids such as, for example, blood and other fluids sensitive to internal friction (=shear stress), the pump head is to be designed such that zones of higher shear forces are avoided as far as possible.

Figure 6:
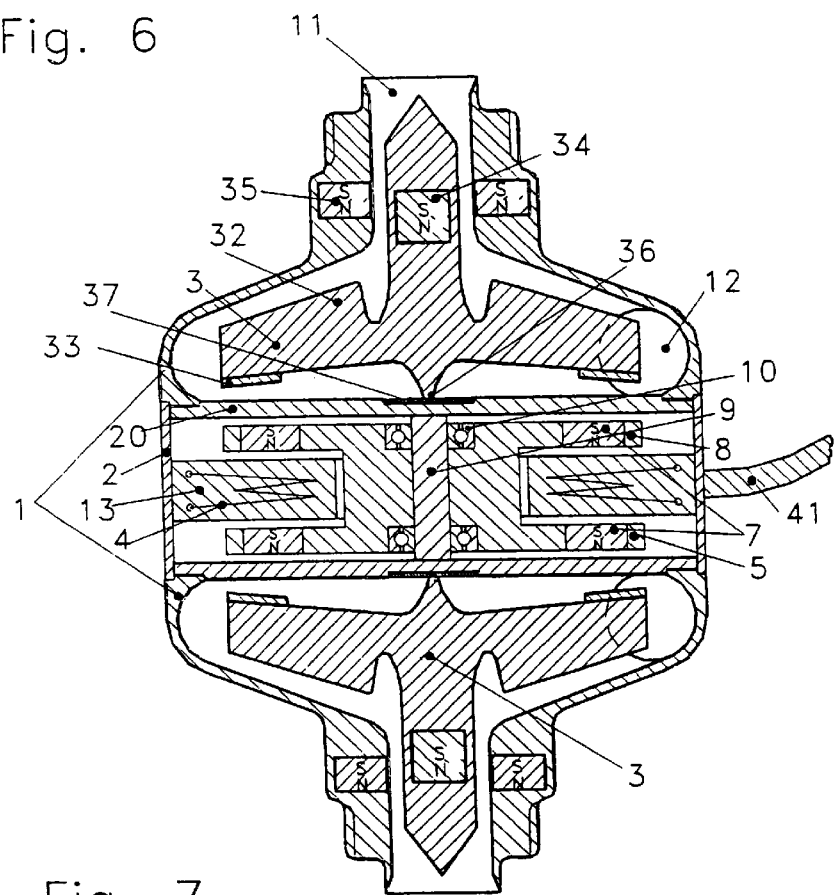
FIG. 6 shows a design with a motor and two pump heads.

Finally, as represented in FIG. 6, the pump can be fitted with two pump heads 1 in order to permit both the left-hand and the right-hand ventricle to be supported by one system. The pump heads and rotors can be designed with a different diameter and/or with a different rotor configuration in order to adapt to the different required pumping capacities of the two ventricles.

As represented in FIGS. 11 to 14, control surfaces 54, 58 can be arranged in the inflow region of the pump an order to enlarge the hydrodynamically active gap between the rotor and housing, and to increase the efficiency. As shown in a lateral view in FIG. 11 and in plan view in FIG. 12, these control surfaces are preferably fitted on the inside of the wall 62 of the pump intake 11, it being possible to pull the magnet 35 forward into the control surfaces in order to shorten the magnetically active air gap or to provide iron yokes 55 for relaying the magnetic field into the vane. These control surfaces 54 can also be set obliquely or be curved in this case in order to improve the hydrodynamic properties.

Figure 11:
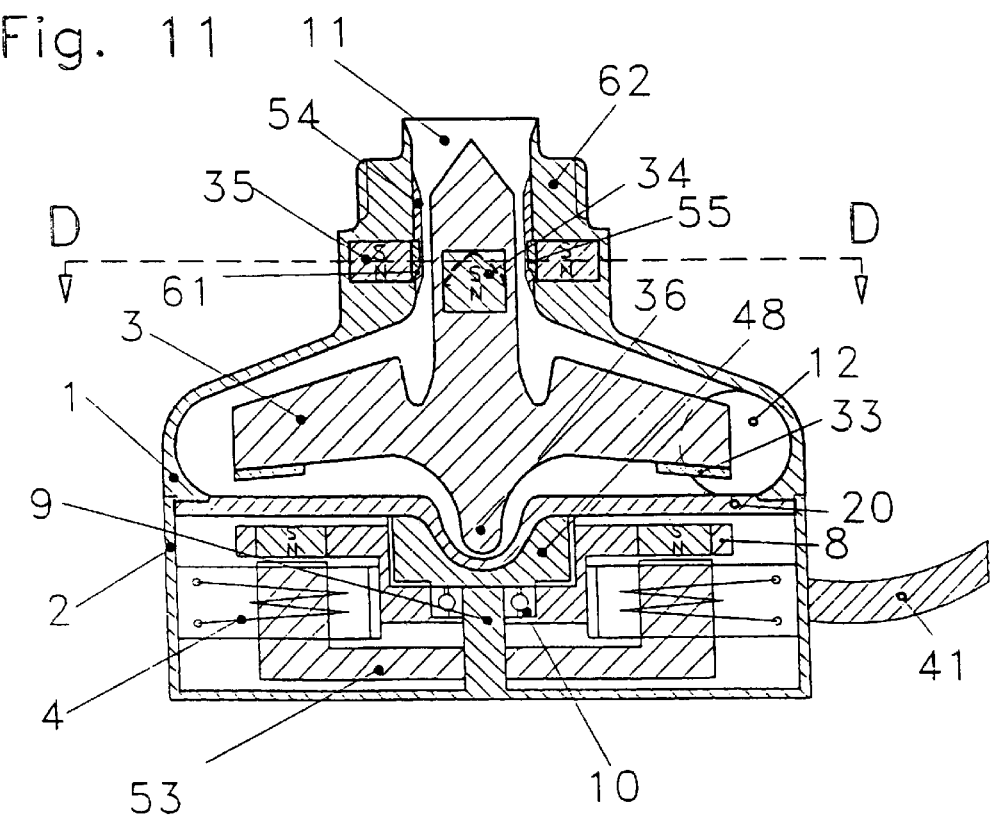
FIG. 11 to FIG. 14 show embodiments for the magnetic bearing of the rotor tip with arrangements of control surfaces either in the pump housing or in the inflow region of the rotor, and a possible multiplication of the magnets in the inflow region.
Figure 12:
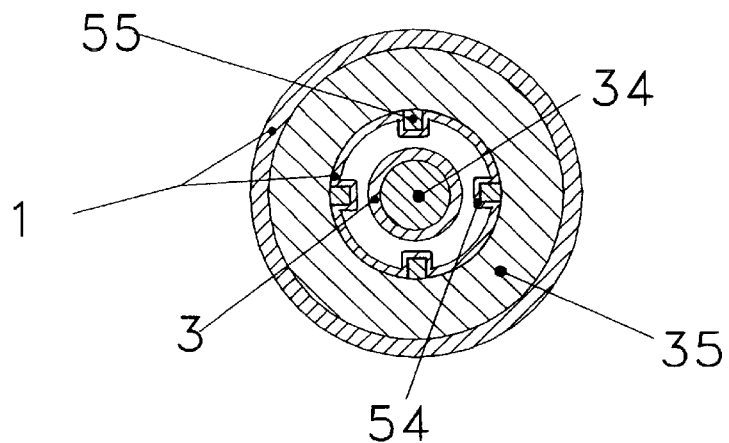

It is shown, moreover, in FIG. 11 that the drive can also be carried out only with a single top rotor disk 8, the magnetic feedback taking place in this case on the rear side of the motor via an annular magnet yoke 53 which interconnects the iron core 45 of the motor coils 14, 16 (see also FIGS. 2a to 3).

Furthermore, as shown in FIG. 11, instead of a straight axially parallel wall the magnets 34, 35 can have an obliquely set or contoured wall in order to achieve a controlled variation of the air gap width, and thus of the magnetically generated restoring force in the case when the rotor is lifted. Given a contoured wall, the magnet 34 can, for example, be domed (indicated by dashes in FIG. 11).

Figure 13:
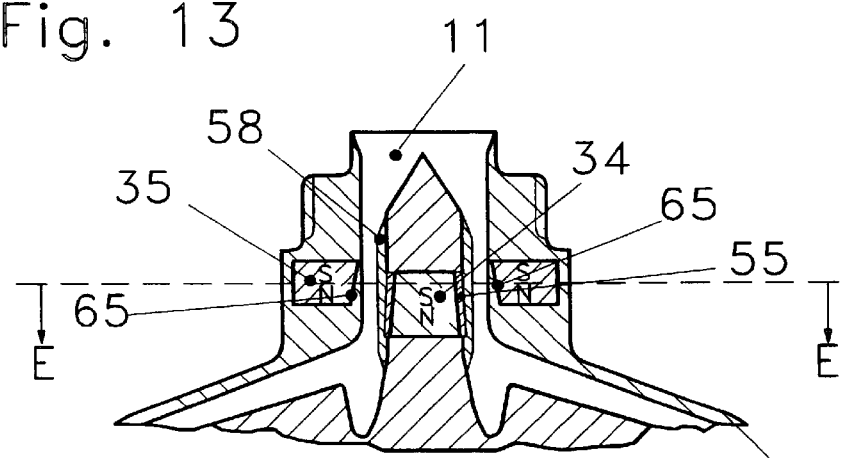
Figure 14:
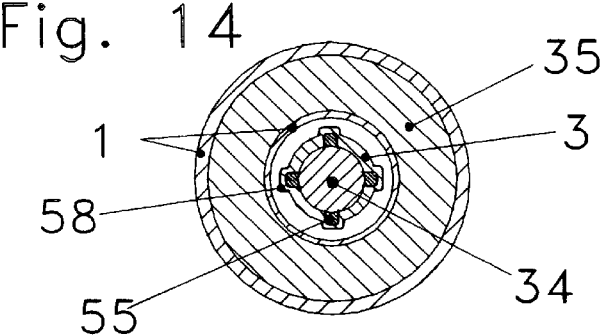

Instead of stationary control surfaces 54 on the pump housing, it is also possible to provide an arrangement of control surfaces 58 on the pump rotor 3 itself, as is represented in FIGS. 13 and 14, it also being possible in this case to provide an extension of the magnet 34 into these control surfaces 58 or iron yokes 55, in order to reduce the magnetically active air gap.

Figure 15:
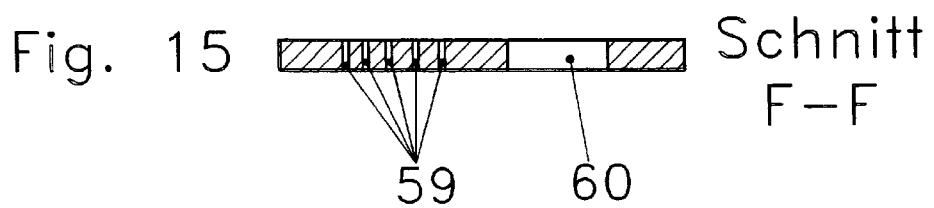
FIGS. 15 and 16 show the plan view of the rear side of the rear wall of the pump head and an or associated cross-section with arranged depressions for minimizing the eddy current losses.
Figure 16:
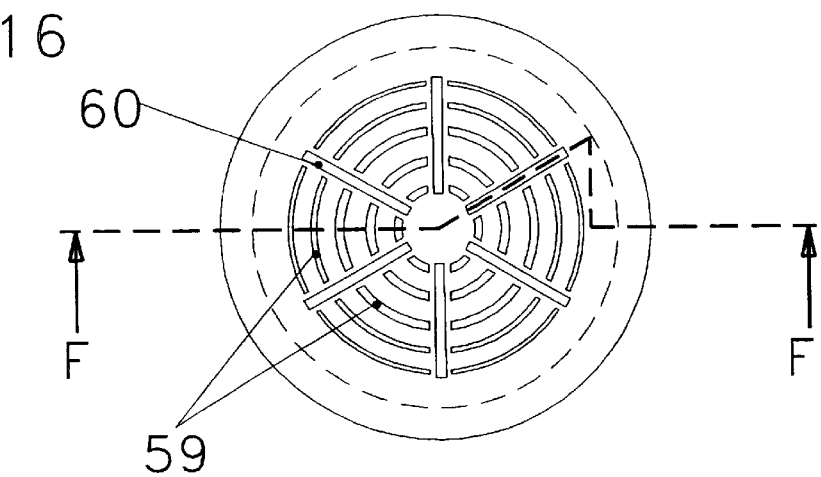

In the case of a metallic rear wall 20 of the pump, which does, after all, simultaneously represent the covering wall of the drive, the moving magnetic field produces eddy currents between the drive rotor disk 8 and permanent magnet 33 of the pump rotor. It is possible for the purpose of reducing these eddy currents to increase the electrical resistance of the rear wall 20 by means of depressions 59. 60, which are represented in FIGS. 15 and 16. These depressions can be provided in a circular arrangement 59 and/or in a radial arrangement 60, it being necessary to take account of the mechanical strength of the pump and of the drive in the case of the number and shaping. If the rear wall of the pump 20 and the covering wall of the drive are of separate design in order to permit the pump and drive to be more easily separated, depressions in the covering wall of the drive can also be designed as slots.

Figure 17:
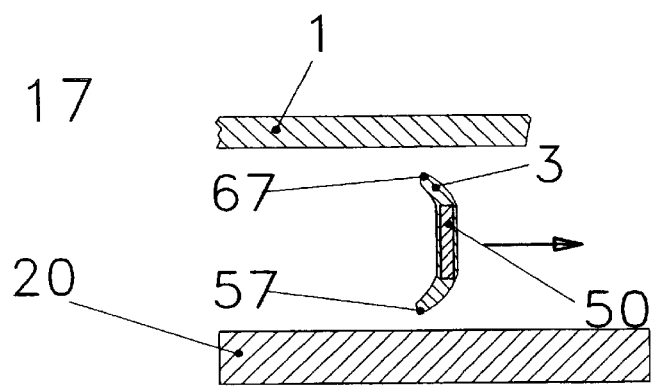
FIG. 17 shows the design of a rotor vane with supporting surface near the base. Finally.

As is shown in FIG. 17, the pump rotor vanes can also be equipped with a supporting surface 57 in the vicinity of the pump base 20, in order to permit a reduction, caused hydrodynamically by the rotation, in the contact pressure in the bearing, or a lifting of the rotor. It is also possible to arrange supporting surfaces 67 on the other side of the pump rotor.

Figure 18:
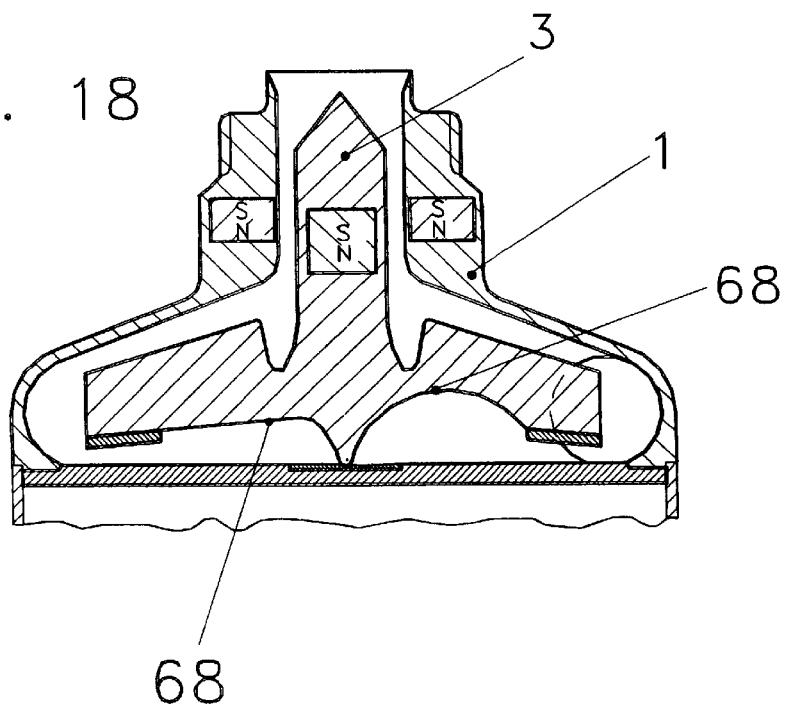
FIG. 18 is a diagram of a rotor with differently shaped vanes for achieving a flow eddy with a center point off the rotor axis.

Finally, it is shown in fig. 18 that in order to achieve an asymmetrical flow near the base, and thus an increase in the washout in the vicinity of the axis, the vanes of the rotor can be of different (asymmetrical) design, it being possible to provide a different height of the vane, but also a different inclination of the vanes (see the different shape of the surfaces 68).

What is claimed is:

1. A centrifugal pump comprising a pump head (1) and a drive (2) for delivering blood and other shear-sensitive fluids, such as cell-containing cleaning suspensions, for example, in blood-cleaning units, wherein the drive (2) has a drive rotor (64) with a rotor disk (8) which is provided with permanent magnets (7) which are assigned permanent magnets (33), fitted on the pump rotor (3), for the purpose of magnetic coupling, and are assigned in the drive to the magnetic coils (4) of a stator for the purpose of generating the rotary movement, and wherein the pump rotor axis (61) extends into the pump intake (11) and is magnetically centered in the pump intake (11).

2. The pump as claimed in claim 1, wherein for the purpose of magnetically centering the pump rotor axis (61) the latter has a permanent magnet (34), and the pump intake (11) has one or more annularly arranged magnets (35) polarized in the same direction.

3. The pump as claimed in claim 2, wherein the magnets (35) are permanent magnets.

4. The pump as claimed in claim 2, wherein the magnets (35) are electromagnets.

5. The pump as claimed in claim 1, wherein the magnets (35) are arranged in the wall (62) of the pump intake (11), and an annular flow channel (63) is formed between the pump rotor axis (61) and the wall of the pump intake (11).

6. The pump as claimed in claim 1, wherein the permanent magnet (34) on the pump rotor axis (61) or the pump rotor (3) is offset in the axial direction with respect to the annularly arranged magnets (35) of the pump intake (11), in order to increase the centering effect.

7. The pump as claimed in claim 1, wherein controls (54, 58) are arranged on the wall (62) of the pump intake (11) or on the pump rotor axis (61), magnets (34 or 35) or their yoke projecting if appropriate into the region of the control surfaces (54, 58).

8. The pump as claimed in claim 1, wherein one or both magnets (34 or 35) of the pump intake have oblique or contoured surfaces (65) on their sides facing one another.

9. The pump as claimed in claim 1, wherein the direction of magnetization of the magnets (33) on the pump rotor (3) is aligned transverse to the direction of magnetization of the drive magnets (7) (FIGS. 2a to 3).

10. The pump as claimed in claim 1, wherein the bearing (66) of the pump rotor (3) is constructed as a magnetic bearing on the rear wall (20) of the pump head (1), this bearing comprising one or more permanent magnets (39) in the rear rotor tip (36) on the rear side of the rotor (3) and permanent magnets (47) and/or electromagnets (46) in the bearing shell formed by the rear wall (20) (FIG. 5).

11. The pump as claimed in claim 1, wherein the bearing seat (52) of the pump rear wall (20) is designed with a flat central surface for the rear rotor tip (36), which surface permits lateral excursions of the rear rotor tip in a limited range of typically 0.5 to 3 mm diameter, (FIG. 10).

12. The pump as claimed in claim 1, wherein the pump rotor (3) has on its rear side vanes? (27) which during rotation produce a dynamic pressure by virtue of a different inclination of the vane surfaces on the upstream side (30) and downstream side (31), and thereby facilitate and/or cause lifting of the pump rotor (3) from the rear wall (20) (FIGS. 7, 8).

13. The pump as claimed in claim 1, wherein the pump rotor (3) is designed with exposed rotor vanes (51) in which there are recessed magnets (50) whose magnetization runs transverse to the rotation axis of the pump rotor axis (61) (FIGS. 2b, c).

14. The pump as claimed in claim 1, wherein there are provided on the underside of the rotor vanes (51) support surfaces (57) which cause an axial force during rotation in fluid (FIG. 17).

15. The pump as claimed in claim 1, wherein there are provided on the topside of the rotor vanes (51) support surfaces (67) which cause an axial force during rotation in fluid (FIG. 17).

16. The pump as claimed in claim 1, wherein the rotor vanes have different surfaces (68) and/or angles of attack, and thereby cause an asymmetrical flow on the rear wall of the pump (FIG. 18).

17. The pump as claimed in claim 1, wherein the drive rotor (64) comprises an upper and a lower rotor disk (8, 5), and the magnet coils (4) of the stator are situated between the two rotor disks (5, 8).

18. The pump as claimed in claim 1, wherein for the purpose of reducing the stray magnetic field the lower rotor disk (5) of the drive (2) has a magnetic return path in the form of a magnetically conductive disk or ring (6) made, for example, from soft iron.

19. The pump as claimed in claim 1, wherein for the purpose of improving the efficiency of the drive the coils (14, 15, 16) are arranged in a plurality of offset layers and/or wound inclined to the plane of the coil form (13) (FIGS. 2, 3).

20. The pump as claimed in claim 1, wherein the drive rotor (64) comprises an upper rotor disk, and provided in the stator instead of the lower rotor disk is a magnetic yoke (53) which interconnects the iron cores (45) of the magnet coils (4) of the stator (FIG. 11).

21. The pump as claimed in claim 1, wherein circular and/or radial depressions (59, 60) or also slots are provided in the rear wall of the pump or, in the case of a separable pump and drive, on the covering wall of the drive (FIGS. 15, 16).

22. The pump as claimed in claim 1, wherein in each case a pump head (1) is fitted on both sides of the drive (2) in the axial direction, preferably for the purpose of simultaneously supporting/substituting of the left and right heart, it being possible for the size and rotor configuration of the two pump heads to differ in order to achieve a pumping capacity matched to the physiological requirements.

23. The pump as claimed in claim 1, wherein the pump head (1) and the drive (2) can be separated from one another in order to replace the pump head (1) or the drive (2) alone.

* * * * *